(12) United States Patent
Burwinkel et al.

(10) Patent No.: US 12,177,630 B2
(45) Date of Patent: *Dec. 24, 2024

(54) EAR-WORN ELECTRONIC DEVICE CONFIGURED TO COMPENSATE FOR HUNCHED OR STOOPED POSTURE

(71) Applicant: Starkey Laboratories, Inc., Eden Prairie, MN (US)

(72) Inventors: Justin R. Burwinkel, Eden Prairie, MN (US); Kevin Seitz-Paquette, Minneapolis, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/238,170

(22) Filed: Aug. 25, 2023

(65) Prior Publication Data

US 2023/0403516 A1 Dec. 14, 2023

Related U.S. Application Data

(63) Continuation of application No. 17/603,822, filed as application No. PCT/US2020/057521 on Oct. 27, 2020, now Pat. No. 11,778,392.

(Continued)

(51) Int. Cl.
*H04R 25/00* (2006.01)
*A61B 5/00* (2006.01)
(Continued)

(52) U.S. Cl.
CPC ......... *H04R 25/407* (2013.01); *A61B 5/1071* (2013.01); *A61B 5/1114* (2013.01);
(Continued)

(58) Field of Classification Search
CPC .............. H04R 2225/61; H04R 25/405; H04R 25/407; H04R 25/505; H04R 25/554;
(Continued)

(56) References Cited

U.S. PATENT DOCUMENTS 7,912,237 B2 3/2011 Fischer
9,094,769 B2 7/2015 Bisgaard
(Continued)

FOREIGN PATENT DOCUMENTS

DE 102006028862 1/2008
DE 102015219581 11/2016
(Continued)

OTHER PUBLICATIONS

International Search Report and Written Opinion from PCT Application No. PCT/2020/057521, dated Apr. 6, 2021, 20 pages.

*Primary Examiner* — Phylesha Dabney
(74) *Attorney, Agent, or Firm* — Mueting Raasch Group

(57) ABSTRACT

A hearing device comprises a processor operatively coupled to memory, a speaker or a receiver, and one or both of a microphone arrangement and a telecoil arrangement. A sensor is operatively coupled to the processor and configured to sense an angular position of the device relative to a horizontal plane oriented orthogonal to a direction of gravity. The processor is configured to detect a change in the angular position of the device from a first angular position to a second angular position, the first angular position corresponding to a specified angular position that provides for a target or optimal level of device performance and the second angular position resulting in suboptimal device performance. The processor is also configured to implement a corrective action that improves performance of the device relative to the suboptimal device performance while operating the device at the second angular position.

21 Claims, 10 Drawing Sheets

Related U.S. Application Data

(60) Provisional application No. 62/935,361, filed on Nov. 14, 2019.

(51) Int. Cl.
  *A61B 5/107* (2006.01)
  *A61B 5/11* (2006.01)
  *G01B 21/22* (2006.01)
  *G08B 7/00* (2006.01)

(52) U.S. Cl.
  CPC .......... *A61B 5/6817* (2013.01); *A61B 5/7405* (2013.01); *A61B 5/7455* (2013.01); *G01B 21/22* (2013.01); *H04R 25/405* (2013.01); *H04R 25/505* (2013.01); *H04R 25/603* (2019.05); *H04R 25/604* (2013.01); *H04R 25/609* (2019.05); *A61B 2560/0257* (2013.01); *A61B 2562/0219* (2013.01); *G08B 7/00* (2013.01); *H04R 2225/61* (2013.01)

(58) Field of Classification Search
  CPC .. H04R 25/603; H04R 25/604; H04R 25/609; A61B 2560/0257; A61B 2562/0219; A61B 5/1071; A61B 5/1114; A61B 5/6817; A61B 5/7405; A61B 5/7455
  USPC .......................................................... 381/313
  See application file for complete search history.

(56) References Cited

U.S. PATENT DOCUMENTS

| | | |
|---|---|---|
| 2003/0005907 A1 | 1/2003 | Nakakita |
| 2008/0192968 A1 | 8/2008 | Ho |
| 2010/0074460 A1 | 3/2010 | Marzetta |
| 2013/0195296 A1 | 8/2013 | Merks |
| 2013/0343584 A1* | 12/2013 | Bennett ............... A61J 1/00 381/317 |
| 2013/0343585 A1* | 12/2013 | Bennett ............... H04W 4/80 381/317 |
| 2016/0112811 A1* | 4/2016 | Jensen ............... G10L 21/0232 381/17 |
| 2017/0174237 A1 | 6/2017 | Kintz |
| 2017/0272867 A1 | 9/2017 | Zisapel |
| 2019/0011643 A1 | 1/2019 | Otomitsu |
| 2022/0174428 A1* | 6/2022 | Hoang ............... H04R 25/552 |

FOREIGN PATENT DOCUMENTS

| | | |
|---|---|---|
| EP | 1956867 | 8/2008 |
| EP | 3264798 | 1/2018 |
| EP | 3285501 | 2/2018 |

* cited by examiner

EAR-WORN ELECTRONIC DEVICE CONFIGURED TO COMPENSATE FOR HUNCHED OR STOOPED POSTURE

RELATED PATENT APPLICATIONS

This application is a continuation application of U.S. application Ser. No. 17/603,822, filed Oct. 14, 2021, which is a U.S. National Stage application under 35 U.S.C. 371 of PCT Application No. PCT/US2020/057521, filed Oct. 27, 2020, and which claims priority to U.S. Provisional Application No. 62/935,361, filed Nov. 14, 2019, the contents of which are hereby incorporated by reference in their entireties.

TECHNICAL FIELD

This application relates generally to ear-worn electronic devices, including hearing devices, hearing aids, personal amplification devices, and other hearables.

BACKGROUND

Hearing devices provide sound for the wearer. Some examples of hearing devices are headsets, hearing aids, speakers, cochlear implants, bone conduction devices, and personal listening devices. For example, hearing aids provide amplification to compensate for hearing loss by transmitting amplified sounds to a wearer's ear canals. Hearing devices can include components which are orientation-dependent and designed for optimal operation when worn by a wearer having normal posture. Suboptimal performance results when a hearing device with orientation-dependent components is worn by a user with hunched or stooped posture.

SUMMARY

Embodiments are directed to a method implemented by an ear-worn electronic device situated in, on, or about an ear of a wearer. The method comprises sensing an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane. The method also comprises detecting a change in the angular position of the device from a first angular position to a second angular position, the first angular position corresponding to a specified angular position that provides for a target or optimal level of device performance and the second angular position resulting in suboptimal device performance. The method further comprises implementing, by the device, a corrective action that improves performance of the device relative to the suboptimal device performance while operating the device at the second angular position. For example, the corrective action can improve device performance from suboptimal device performance to about the target or optimal level when operating the hearing device at the second angular position.

Embodiments are directed to an ear-worn electronic hearing device configured for use in, on, or about an ear of a wearer. The device comprises a processor operatively coupled to memory, a speaker or a receiver operatively coupled to the processor, and one or both of a microphone arrangement and a telecoil arrangement operatively coupled to the processor. A sensor is operatively coupled to the processor and configured to sense an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane. The processor is configured to detect a change in the angular position of the device from a first angular position to a second angular position, the first angular position corresponding to a specified angular position that provides for a target or optimal level of device performance and the second angular position resulting in suboptimal device performance. The processor is also configured to implement a corrective action that improves performance of the device relative to the suboptimal device performance while operating the device at the second angular position. For example, the corrective action can improve device performance from suboptimal device performance to about the target or optimal level when operating the hearing device at the second angular position.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
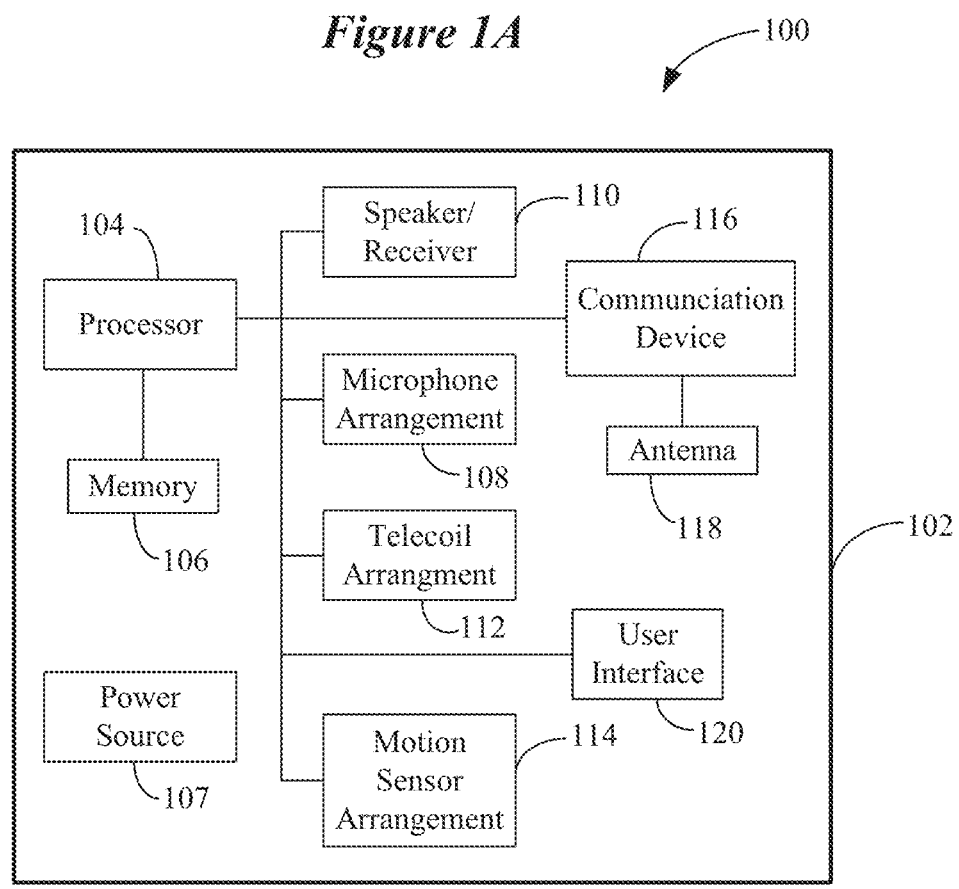
FIG. 1A is a system block diagram of an ear-worn electronic hearing device configured for use in, on, or about an ear of a wearer in accordance with any of the embodiments disclosed herein.

A typical hearing aid includes one or more microphones and can also include a telecoil. A telecoil is a device comprising a tiny coil of wire wound around a core that induces an electric current in the coil when in the presence of a changing magnetic field. A telecoil can serve as an alternate or supplemental input device for a hearing aid. For example, a telecoil can be used as an input source instead of, or in addition to, the microphone(s), allowing the hearing aid to receive a magnetic signal which represents sound.

A hearing aid's microphones and telecoils are, by design, oriented for users with typical posture. As such, users with hunched or stooped posture, referred to as kyphosis, often experience diminished hearing aid performance. For example, directional microphones are intended to allow the user to focus on speech originating from an individual who is facing the user. However, users with kyphosis tend to face downward towards their feet instead of towards their communication partner.

Similarly, the orientation of a hearing aid telecoil has a direct relationship with respect to the sensitivity that the telecoil will have to a magnetic field emanating from the horizontal plane. Specifically, if a telecoil is oriented 45 degrees from its optimal position (e.g., due to the user's hunched or stooped posture), the hearing aid will receive a 3 dB lower input. A 60 degree departure from a telecoil's optimal position will result in a 6 dB lower input, and a 90 degree departure can result in a zero or near-zero input.

These positional effects are exacerbated by telecoil positioning within the hearing aid, since the telecoil is often mounted at an angled inside the hearing aid by 15-45 degrees. In an extreme case, a user could tilt their head 30 degrees, but effectively have their telecoil positioned 75 degrees from the optimal position due to kyphosis. Improper hearing aid fittings (such as those that might be performed via an over-the-counter or door-to-door distribution channel) can result in the hearing aid resting on the ear in a suboptimal orientation. For example, if a receiver wire or tubing of a hearing aid is too short, then the device may be oriented excessively downward. If too long, then the device may be oriented excessively upward. Both of these scenarios can result in diminished performance characteristics, similar those described above.

Embodiments of the disclosure are directed to various methods and apparatuses for enhancing or optimizing the performance of a hearing device based on the angular position of the hearing device. The angular position of a hearing device can be monitored using one or more sensors (e.g., accelerometer, gyroscope, magnetometer, inertial measurement unit (IMU), etc.), and compared to the orientation for which the device was designed to performed most optimally. In some embodiments, a measurement of SNR or signal strength of one or more of a microphone(s), a telecoil(s) or other magnetic sensor(s) may be used to determine that the hearing device is in a suboptimal position.

In some embodiments, the hearing device may provide guidance to the user which helps the user to position the hearing device in a more optimal position. For example, when the signal strength is below a threshold or a motion sensor of the hearing device (e.g., one or more IMU sensors) detects head tilt beyond a certain level, then the hearing device can be configured to provide instructions to the user to e.g., "tilt your head upward to improve your listening experience." Various methods of notification are contemplated, including auditory, haptic, and visual notifications. Messages may be delivered through the hearing device or by an operatively connected device, e.g. smartwatch, smartphone, etc.

In some embodiments, parameters of a signal processing algorithm can be adapted such that a polar pattern of a multiplicity of microphones (e.g., a microphone array) may be optimized for a given orientation. In some embodiments, frequency shaping may occur. In some embodiments, parameters of a noise reduction or speech enhancement algorithm may be adapted to attempt to recapture the amount of noise reduction/speech enhancement that is provided through an optimal directional microphone/telecoil orientation.

It is understood that the embodiments described herein may be used with any ear-worn or ear-level electronic device without departing from the scope of this disclosure. The devices depicted in the figures are intended to demonstrate the subject matter, but not in a limited, exhaustive, or exclusive sense. Ear-worn electronic hearing devices (referred to herein as "hearing devices") typically include an enclosure, such as a housing or shell, within or on which internal components are disposed. Typical components of a hearing device can include a processor (e.g., a digital signal processor or DSP), memory circuitry, power management circuitry, one or more communication devices (e.g., a radio, a near-field magnetic induction (NFMI) device), one or more antennas, one or more microphones, one or more telecoils, and a receiver/speaker, for example. Hearing devices can incorporate a long-range communication device, such as a Bluetooth® transceiver or other type of radio frequency (RF) transceiver. A communication device (e.g., a radio or NFMI device) of a hearing device can be configured to facilitate communication between a left ear device and a right ear device of the hearing device. Hearing devices can also incorporate a motion sensor or sensors that can be used to switch input between left and right hearing devices (e.g., assuming left and right devices have varying orientation of the motion sensor(s), such as a telecoil) so that optimal audio can be sent to the opposite hearing device.

Hearing devices of the present disclosure can incorporate an antenna operatively coupled to a high-frequency transceiver, such as a 2.4 GHz radio. The RF transceiver can conform to an IEEE 802.11 (e.g., WiFi®) or Bluetooth® (e.g., BLE, Bluetooth® 4.2, 5.0, or later) specification, for example. It is understood that hearing devices of the present disclosure can employ other transceivers or radios, such as a 900 MHz radio. Hearing devices of the present disclosure can be configured to receive streaming audio (e.g., digital audio data or files) from an electronic or digital source. Representative electronic/digital sources (e.g., accessory devices) include an assistive listening system, a TV streamer, a TV, a radio, a smartphone, a laptop, a cell phone/entertainment device (CPED), a consumer electronic device, or other electronic device that serves as a source of digital audio data or other types of data files. Hearing devices of the present disclosure can be configured to effect bi-directional communication (e.g., wireless communication) of data with an external source, such as a remote server via the Internet or other communication infrastructure. Hearing devices that include a left ear device and a right ear device can be configured to effect bi-directional communication (e.g., wireless communication) therebetween, so as to implement ear-to-ear communication between the left and right ear devices.

The term hearing device of the present disclosure refers to a wide variety of ear-level electronic devices that can aid a person with impaired hearing. The term hearing device also refers to a wide variety of devices that can produce processed sound for persons with normal hearing. Hearing devices of the present disclosure include hearables (e.g., wearable earphones, headphones, earbuds, audio monitors, virtual reality headsets), hearing aids (e.g., hearing instruments), cochlear implants, and bone-conduction devices, for example. Hearing devices include, but are not limited to, behind-the-ear (BTE), in-the-ear (ITE), in-the-canal (ITC), invisible-in-canal (IIC), receiver-in-canal (RIC), receiver-in-the-ear (RITE) or completely-in-the-canal (CIC) type hearing devices or some combination of the above. Throughout this disclosure, reference is made to a "hearing device," which is understood to refer to a system comprising a single left ear device, a single right ear device, or a combination of a left ear device and a right ear device.

Embodiments of the disclosure are defined in the claims. However, below there is provided a non-exhaustive listing of non-limiting examples. Any one or more of the features of these examples may be combined with any one or more features of another example, embodiment, or aspect described herein.

Example Ex1. An ear-worn electronic hearing device configured for use in, on, or about an ear of a wearer, the device comprising a processor operatively coupled to memory, a speaker or a receiver operatively coupled to the processor, one or both of a microphone arrangement and a telecoil arrangement operatively coupled to the processor, and a sensor operatively coupled to the processor and configured to sense an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane. The processor is configured to detect a change in the angular position of the device from a first angular position to a second angular position, the first angular position corresponding to a specified angular position that provides for a target or optimal level of device performance and the second angular position resulting in suboptimal device performance, and implement a corrective action that improves performance of the device relative to the suboptimal device performance while operating the device at the second angular position.

Example Ex2. The device according to Ex1, wherein the processor is configured to determine the first angular position of the device by determining orientation of the wearer's head in a direction substantially along the horizontal plane, and determine the second angular position of the device by determining the orientation of the wearer's head in a direction towards the ground.

Example Ex3. The device according to Ex1 or Ex2, wherein the processor is configured to compare one or more performance parameters of the device at the second angular position to corresponding one or more performance parameters of the device associated with the target or optimal level of device performance, and implement the corrective action in response to the comparison crossing a predetermined threshold.

Example Ex4. The device according to one or more of Ex1 to Ex3, wherein the processor is configured to implement the corrective action by one or more of changing a directional polar pattern of a microphone array of the microphone arrangement, activating selected microphones of the microphone arrangement as a function of angular position of the device, altering a mathematical weighting of one or more of microphone inputs as a function of angular position of the device, receiving signals from selected telecoils of the telecoil arrangement as a function of angular position of the device, altering a mathematical weighting of signals produced by at least two telecoils as a function of angular position of the device, selectively receiving signals from any of one or more microphones and any of one or more telecoils as a function of angular position of the device, and altering a mathematical weighting of signals produced by any of one or more microphones and any one or more telecoils as a function of angular position of the device;

Example Ex5. The device according to Ex1, wherein the device comprises first and second microphones situated on a first plane of the device and a third microphone situated on a second plane of the device transverse to the first plane, the processor is configured to implement the corrective action by summing signals produced by the first, second, and third microphones as a function of angular position of the device, and contribution to the summed signals by the third microphone increases as the angular position of the device changes from the first angular position towards the second angular position.

Example Ex6. The device according to Ex1, wherein the device comprises the telecoil arrangement and the microphone arrangement, and the processor is configured to implement the corrective action by operating the device exclusively or predominately in a telecoil mode until the angular position of the device reaches a threshold angular position relative to the horizontal plane, switching from the telecoil mode to an acoustic microphone mode and operating the device exclusively or predominately in the acoustic microphone mode in response to the angular position of the device exceeding the threshold angular position, and switching from the acoustic microphone mode to the telecoil mode and operating the device exclusively or predominately in a telecoil mode in response to the angular position of the device no longer exceeding the threshold angular position.

Example Ex7. The device according to one or more of Ex1 to Ex6, wherein the processor is configured to implement the corrective action by one of more of generating an audible alert prompting the wearer to change the angular direction of the device towards the horizontal plane, generating a tactile alert prompting the wearer to change the angular direction of the device towards the horizontal plane, and generating an alert signal indicating a need to change the angular direction of the device towards the horizontal plane and transmitting the alert signal to a portable electronic device attached to or situated in proximity to the wearer.

Example Ex8. The device according to one or more of Ex1 to Ex7, wherein the processor is configured to implement the corrective action by one or more of performing frequency shaping on signals produced by one or both of the microphone arrangement and the telecoil arrangement of the device, performing frequency filtering on signals produced by one or both of the microphone arrangement and the telecoil arrangement of the device, adjusting one or more parameters of a noise reduction system of the device, and adjusting one or more parameters of a speech enhancement system of the device.

Example Ex9. The device according to one or more of Ex1 to Ex8, wherein the sensor comprises one or more of one or more inertial sensors, one or more magnetic sensors, an altimeter or a barometer implemented by the processor configured to process microphone signals to detect changes in altitude or barometric pressure between microphones of the microphone arrangement, and the processor configured to sense changes in signal strength or signal-to-noise ratio using signals produced by the microphone arrangement, the telecoil arrangement or the sensor of the device.

Example Ex10. The device according to one or more of Ex1 to Ex9, wherein the processor is configured to determine the angular position of the device using one or both of a positional sensor and a motion sensor.

Example Ex11. A method implemented by an ear-worn electronic device situated in, on, or about an ear of a wearer, the method comprising sensing an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane; detecting a change in the angular position of the device from a first angular position to a second angular position, the first angular position corresponding to a specified angular position that provides for a target or optimal level of device performance and the second angular position resulting in suboptimal device performance; and implementing, by the device, a corrective action that improves performance of the device relative to the suboptimal device performance while operating the device at the second angular position.

Example Ex12. The method according to Ex11, wherein the first angular position of the device is determined by the orientation of the wearer's head in a direction substantially along the horizontal plane, and the second angular position of the device is determined by the orientation of the wearer's head in a direction towards the ground.

Example Ex13. The method according to Ex11 or Ex12, comprising comparing one or more performance parameters of the device at the second angular position to corresponding one or more performance parameters of the device associated with the target or optimal level of device performance, and implementing the corrective action by the device in response to the comparison crossing a predetermined threshold.

Example Ex14. The method according to one or more of Ex11 to Ex13, wherein implementing the corrective action comprises one or more of changing a directional polar pattern of a microphone array of the microphone arrangement, activating selected microphones of the microphone arrangement as a function of angular position of the device, altering a mathematical weighting of one or more of microphone inputs as a function of angular position of the device, receiving signals from selected telecoils of the telecoil arrangement as a function of angular position of the device, altering a mathematical weighting of signals produced by at least two telecoils as a function of angular position of the device, selectively receiving signals from any of one or more microphones and any of one or more telecoils as a function of angular position of the device, and altering a mathematical weighting of signals produced by any of one or more microphones and any one or more telecoils as a function of angular position of the device; Example Ex15. The method according to one or more of Ex11 to Ex14, wherein implementing the corrective action comprises one or more of generating an audible alert prompting the wearer to change the angular direction of the device towards the horizontal plane, generating a tactile alert prompting the wearer to change the angular direction of the device towards the horizontal plane, and generating an alert signal indicating a need to change the angular direction of the device towards the horizontal plane and transmitting the alert signal to a portable electronic device attached to or situated in proximity to the wearer.

FIG. 1A is a system block diagram of an ear-worn electronic hearing device configured for use in, on, or about an ear of a wearer in accordance with any of the embodiments disclosed herein. The hearing device 100 shown in FIG. 1A can represent a single hearing device configured for monaural or single-ear operation or one of a pair of hearing devices configured for binaural or dual-ear operation (see e.g., FIG. 1B). The hearing device 100 shown in FIG. 1A includes a housing 102 within or on which various components are situated or supported.

The hearing device 100 includes a processor 104 operatively coupled to memory 106. The processor 104 can be implemented as one or more of a multi-core processor, a digital signal processor (DSP), a microprocessor, a programmable controller, a general-purpose computer, a special-purpose computer, a hardware controller, a software controller, a combined hardware and software device, such as a programmable logic controller, and a programmable logic device (e.g., FPGA, ASIC). The processor 104 can include or be operatively coupled to memory 106, such as RAM, SRAM, ROM, or flash memory. In some embodiments, processing can be offloaded or shared between the processor 104 and a processor of a peripheral or accessory device.

A microphone arrangement 108 is operatively coupled to the processor 104. The microphone arrangement 108 can include one or more discrete microphones or a microphone array(s) (e.g., configured for microphone array beamforming). Each of the microphones of the microphone arrangement 108 can be situated at different locations of the housing 102. It is understood that the term microphone used herein can refer to a single microphone or multiple microphones unless specified otherwise. The microphones of the microphone arrangement 108 can be any microphone type. In some embodiments, the microphones are omnidirectional microphones. In other embodiments, the microphones are directional microphones. In further embodiments, the microphones are a combination of one or more omnidirectional microphones and one or more directional microphones. One, some, or all of the microphones can be microphones having a cardioid, hypercardioid, supercardioid or lobar pattern, for example. One, some, or all of the microphones can be multi-directional microphones, such as bidirectional microphones. One, some, or all of the microphones can have variable directionality, allowing for real-time selection between omnidirectional and directional patterns (e.g., selecting between omni, cardioid, and shotgun patterns). In some embodiments, the polar pattern(s) of one or more microphones of the microphone arrangement 108 can vary depending on the frequency range (e.g., low frequencies remain in an omnidirectional pattern while high frequencies are in a directional pattern).

Depending on the hearing device implementation, different microphone technologies can be used. For example, the hearing device 100 can incorporate any of the following microphone technology types (or combination of types): MEMS (micro-electromechanical system) microphones (e.g., capacitive, piezoelectric MEMS microphones), moving coil/dynamic microphones, condenser microphones, electret microphones, ribbon microphones, crystal/ceramic microphones (e.g., piezoelectric microphones), boundary microphones, PZM (pressure zone microphone) microphones, and carbon microphones.

A telecoil arrangement 112 is operatively coupled to the processor 104, and includes one or more (e.g., 1, 2, 3, or 4) telecoils. It is understood that the term telecoil used herein can refer to a single telecoil or magnetic sensor or multiple telecoils or magnetic sensors unless specified otherwise. Also, the term telecoil can refer to an active (powered) telecoil or a passive telecoil (which only transforms received magnetic field energy). The telecoils of the telecoil arrangement 112 can be positioned within the housing 102 at different angular orientations. The hearing device 100 includes a speaker or a receiver 110 capable of transmitting sound from the hearing device 100 to the wearer's ear drum. A power source 107 provides power for the various components of the hearing device 100. The power source 107 can include a rechargeable battery (e.g., lithium-ion battery), a conventional battery, and/or a supercapacitor arrangement.

The hearing device 100 also includes a motion sensor arrangement 114. The motion sensor arrangement 114 includes one or more sensors configured to sense motion and/or a position of the wearer of the hearing device 100. The motion sensor arrangement 114 can comprise one or more of an inertial measurement unit or IMU, an accelerometer(s), a gyroscope(s), a nine-axis sensor, a magnetometer(s) (e.g., a compass), and a GPS sensor. The IMU can be of a type disclosed in commonly owned U.S. Pat. No. 9,848,273, which is incorporated herein by reference. In some embodiments, the motion sensor arrangement 114 can comprise two microphones of the hearing device 100 (e.g., microphones of left and right hearing devices 100) and software code executed by the processor 104 to serve as altimeters or barometers. The processor 104 can be configured to compare small changes in altitude/barometric pressure using microphone signals to determine orientation (e.g., angular position) of the hearing device 100. For example, the processor 104 can be configured to sense the angular position of the hearing device 100 by processing microphone signals to detect changes in altitude or barometric pressure between microphones of the microphone arrangement 108.

The hearing device 100 can incorporate an antenna 118 operatively coupled to a communication device 116, such as a high-frequency radio (e.g., a 2.4 GHz radio). The radio(s) of the communication device 116 can conform to an IEEE 802.11 (e.g., WiFi®) or Bluetooth® (e.g., BLE, Bluetooth® 4.2, 5.0, 5.1 or later) specification, for example. It is understood that the hearing device 100 can employ other radios, such as a 900 MHz radio. In addition, or alternatively, the hearing device 100 can include a near-field magnetic induction (NFMI) sensor for effecting short-range communications (e.g., ear-to-ear communications, ear-to-kiosk communications).

The antenna 118 can be any type of antenna suitable for use with a particular hearing device 100. A representative list of antennas 118 include, but are not limited to, patch antennas, planar inverted-F antennas (PIFAs), inverted-F antennas (IFAs), chip antennas, dipoles, monopoles, dipoles with capacitive-hats, monopoles with capacitive-hats, folded dipoles or monopoles, meandered dipoles or monopoles, loop antennas, Yagi-Udi antennas, log-periodic antennas, and spiral antennas. Many of these types of antenna can be implemented in the form of a flexible circuit antenna. In such embodiments, the antenna 118 is directly integrated into a circuit flex, such that the antenna 118 does not need to be soldered to a circuit that includes the communication device 116 and remaining RF components.

The hearing device 100 also includes a user interface 120 operatively coupled to the processor 104. The user interface 120 is configured to receive an input from the wearer of the hearing device 100. The input from the wearer can be a touch input, a gesture input, or a voice input. The user interface 120 can include one or more of a tactile interface, a gesture interface, and a voice command interface. The tactile interface can include one or more manually actuatable switches (e.g., a push button, a toggle switch, a capacitive switch). For example, the user interface 120 can include a number of manually actuatable buttons or switches, at least one of which can be used by the wearer when customizing the directionality of the microphones 108.

Figure 2:
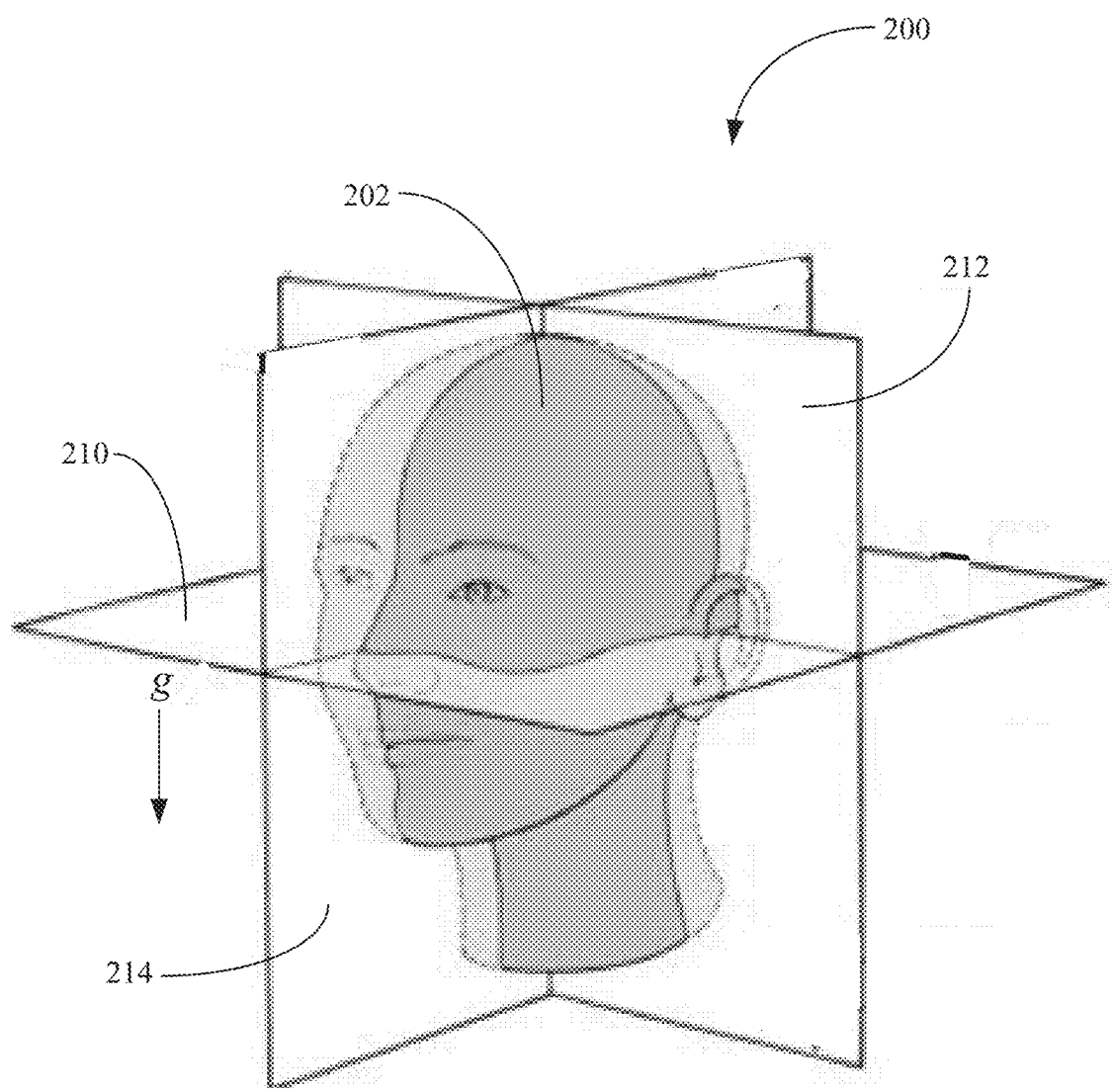
FIG. 2 shows the anatomical planes of a head of a hearing device wearer for purposes of illustration.

As was discussed previously, embodiments of the disclosure are directed to various methods and apparatuses for optimizing the performance of a hearing device based on the angular position of the hearing device. To facilitate an understanding of various embodiments, reference is made to FIG. 2 which shows the anatomical planes 200 of a head 202 of a hearing device wearer. An anatomical plane is a hypothetical plane used to transect the wearer's head in order to describe the movements of the wearer's head. FIG. 2 shows a horizontal plane 210, also referred to as a transverse or axial plane. In the description of various embodiments, the horizontal plane 210 refers to a reference plane which is oriented orthogonal to a direction of gravity. FIG. 2 also shows a longitudinal plane 214, also referred to as a median or sagittal plane. The longitudinal plane 214 is orthogonal to the horizontal plane 210 and divides the head into left and right portions. FIG. 2 further shows a frontal plane 212, also referred to as the coronal plane. The frontal plane 212, which is orthogonal to the longitudinal plane 214 and the horizontal plane 210, divides the head into back and front portions.

Movement of the wearer's head 102 is based on movements of the wearer's neck. There are six movements of the human neck. A first neck movement is referred to as flexion, which is movement in which the chin is lowered down towards the chest. A second neck movement is referred to as extension, in which the neck is extended, as in looking upward toward the ceiling. The third and fourth neck movements are lateral rotation to the left and lateral rotation to the right (direct lateral rotation to either side). The fifth and sixth neck movements are lateral flexion, which may be described as trying to place the ear upon the shoulder through a sideways movement of the neck, directing that ear toward the shoulder tip on both sides. Embodiments of the disclosure are directed to sensing and correcting for the angular position of a hearing device due largely to flexion and extension motions of the wearer's neck and, to a lesser degree, lateral flexion and lateral extension of the wearer's neck.

Figure 1B:
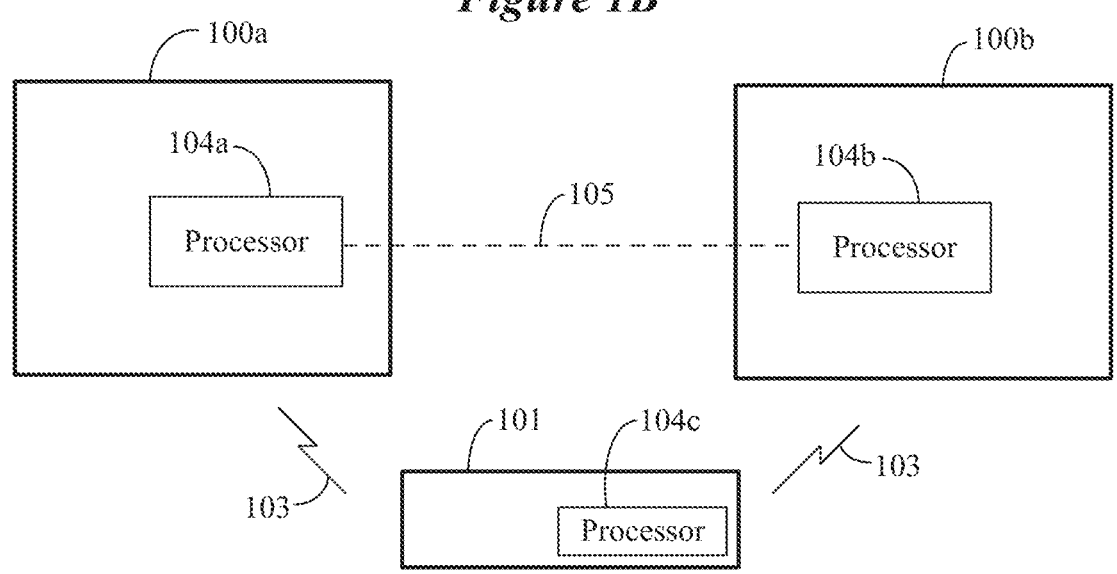
FIG. 1B is a system block diagram of two ear-worn electronic hearing devices configured for use in, on, or about left and right ears of a wearer in accordance with any of the embodiments disclosed herein.

In accordance with any of the embodiments disclosed herein, and with further reference to FIGS. 1A, 1B, and 2, an ear-worn electronic hearing device 100 is configured for use in, on, or about an ear of a wearer and comprises a processor 104 operatively coupled to memory 106. A speaker or a receiver 110 is operatively coupled to the processor 104. One or both of a microphone arrangement 108 and a telecoil arrangement 112 is operatively coupled to the processor 104. A motion sensor 114 is operatively coupled to the processor 104 and configured to sense an angular position of the device 100 relative to a horizontal plane 210 oriented orthogonal to a direction of gravity, g. The angular position of the hearing device 100 substantially corresponds to an orientation of the wearer's head relative to the horizontal plane 210, a longitudinal plane 212 orthogonal to the horizontal plane 210, and a frontal plane 212 orthogonal to the horizontal plane 210 and the longitudinal plane 214.

According to disclosed embodiments, the processor 104 is configured to detect a change in the angular position of the hearing device 100 from a first angular position to a second angular position. The first angular position corresponds to a specified angular position that provides for a prescribed or optimal level (e.g., designed or target level) of hearing device performance, and the second angular position results in suboptimal hearing device performance. The first angular position can be based on how the hearing device 100 is designed and/or calibrated by the manufacturer or how the hearing device 100 has been configured by e.g., an audiologist who has adjusted the hearing device settings for the wearer. For example, through real-ear verification measures, the audiologist may have set the hearing device 100 to provide optimal telecoil audibility for the wearer in their office hearing loop, which in effect corrects for the natural hunch of the user. In this illustrative scenario, if the wearer moves to a "more optimal position" as designed by the manufacturer, the settings could result in audio output that is too loud.

The processor 104 is configured to implement a corrective action that improves performance of the hearing device 100 relative to the suboptimal device performance while operating the hearing device 100 at the second angular position. In some embodiments, one of the processors 104 of a binaural hearing device system (e.g., left or right device processor 104a, 104b) is configured to implement the processes described above and elsewhere herein. In other embodiments, and as shown in FIG. 1B, the processor 104a of a left hearing device 100a and the processor 104b of a right hearing device 100b are configured to cooperate via a communication link 105 (e.g., an RF or NFMI link) to implement the processes described above and elsewhere herein. In further embodiments, one or more of the processors 104a, 104b and a processor or processors 104c of one or more peripheral and/or accessory devices 101 are configured to cooperate via a communication links 105, 103 (e.g., RF and/or NFMI links) to implement the processes described above and elsewhere herein. In some embodiments, the left and right hearing devices 100a, 100b can be configured to communicate through an "Ear-Phone-Ear" pattern by leveraging the peripheral device 104c via communication link(s) 103.

Figure 3A:
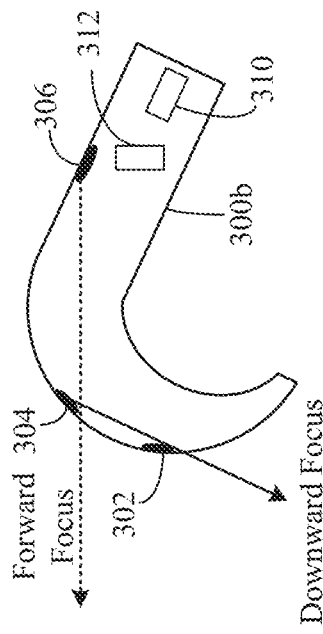
FIG. 3A shows a hearing device oriented in a prescribed (e.g., optimal) angular position for operation when deployed in, on, or about a wearer's ear.
Figure 3B:
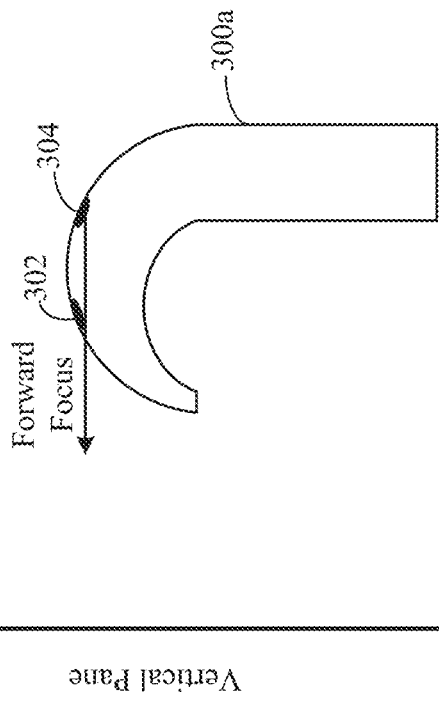
FIG. 3B shows a hearing device oriented in a suboptimal angular position for operation when deployed in, on, or about a wearer's ear, the hearing device configured to provide improved performance when operating in the suboptimal angular position according to any of the disclosed embodiments.

FIG. 3A shows a hearing device 300a oriented in a prescribed (e.g., optimal) angular position for operation when deployed in, on, or about a wearer's ear. The hearing device 300a includes a pair of microphones 302, 304, which may be omnidirectional microphones whose signals may be processed to form a variety of sensitivity patterns. As is shown in FIG. 3A, the prescribed angular position of the hearing device 300a provides for a forward focus of the sensitivity pattern provided by microphones 302, 304. FIG. 3B shows a hearing device 300b in a suboptimal angular position due to flexion of the wearer's neck or hunched or stooped posture of the wearer. As can be seen in FIG. 3B, the suboptimal angular position of the hearing device 300b provides for a downward focus of the sensitivity pattern provided by microphones 302, 304.

According to any of the disclosed embodiments, the hearing device 300b can include one or more additional microphones 306 positioned at a location of the hearing device housing which is out-of-plane with respect to a plane of microphones 302, 304. For example, microphones 302, 304 can be omnidirectional microphones placed on the top of the hearing device 300b (e.g., on the top of a standard BTE-type hearing device). The addition of microphone 306 (e.g., on the back or bottom of a standard BTE-type hearing device) can allow the hearing device 300b to form a polar pattern similar to that provided by device 300a, but at an optimal angle for an individual who is hunching or stooped over. For example, the microphones 302 and 304 are too close to each other along the horizontal plane when in the hearing device 300b is the angular position show in FIG. 3B. Utilizing the additional microphone 306 situated at a location of the hearing device 300b out-of-plane relative to the plane of microphones 302, 304 provides for enhanced or optimal device performance when operating at the suboptimal angular position shown in FIG. 3B.

According to any of the disclosed embodiments, the hearing device 300b can also include one or more telecoils, such as telecoil 310 and 312 shown in FIG. 3B. It is noted that telecoil 310 is oriented within the hearing device 300b to provide prescribed (e.g., optimal) performance when the hearing device 300b is oriented in a prescribed (e.g., optimal) angular position for operation, such as that shown in FIG. 3A. The telecoil 312 is situated within the housing of hearing device 300b so that it is oriented at a more preferred angular position relative to telecoil 310 when the wearer's posture is hunched or stooped or when the wearer's neck is in flexion, as is depicted in FIG. 3B.

In some embodiments, one or more additional telecoils and/or one or more additional microphones can be added as a "module" or "wart" to a standard hearing device (e.g., as an aftermarket option). For example, one or more additional telecoils and/or microphones can be added to a hearing device or devices much like current approaches to attaching a DAI (direct audio input) or programming "boots" to hearing aids.

A hearing device according to any of the embodiments disclosed herein can be configured to switch between a telecoil mode and an acoustic microphone mode depending on the angular position of the hearing device relative to a horizontal plane which is oriented orthogonal to a direction of gravity. For example, the hearing device can be configured to switch from a telecoil mode to an acoustic microphone mode when the hearing device orientation crosses a threshold, such as when the wearer is looking downward. In this illustrative embodiment, the threshold angle can be set such that if the angle of the telecoil in the hearing device relative to the horizontal plane falls below a threshold angle, performance is reduced by an unacceptable degree. To continue to provide sufficient hearing assistance, the hearing device can be configured automatically switch to an acoustic microphone mode, until the angle of the hearing device relative to the horizontal plane is exceeded. In this illustrative example, it is assumed that the threshold angle represents the most extreme acute angle that can be measured in three-dimensional space between the telecoil and the horizontal plane (e.g., ground). In some embodiments, a method of normalizing the audio levels between acoustic and telecoil inputs that are switching adaptively can be implemented by the hearing device, such as in manners disclosed in commonly owned U.S. Patent Application Ser. No. 62/914,771, filed on Oct. 14, 2019, and entitled "HEARING ASSISTANCE SYSTEM WITH AUTOMATIC HEARING LOOP MEMORY," which is incorporated herein by reference.

Figure 4:
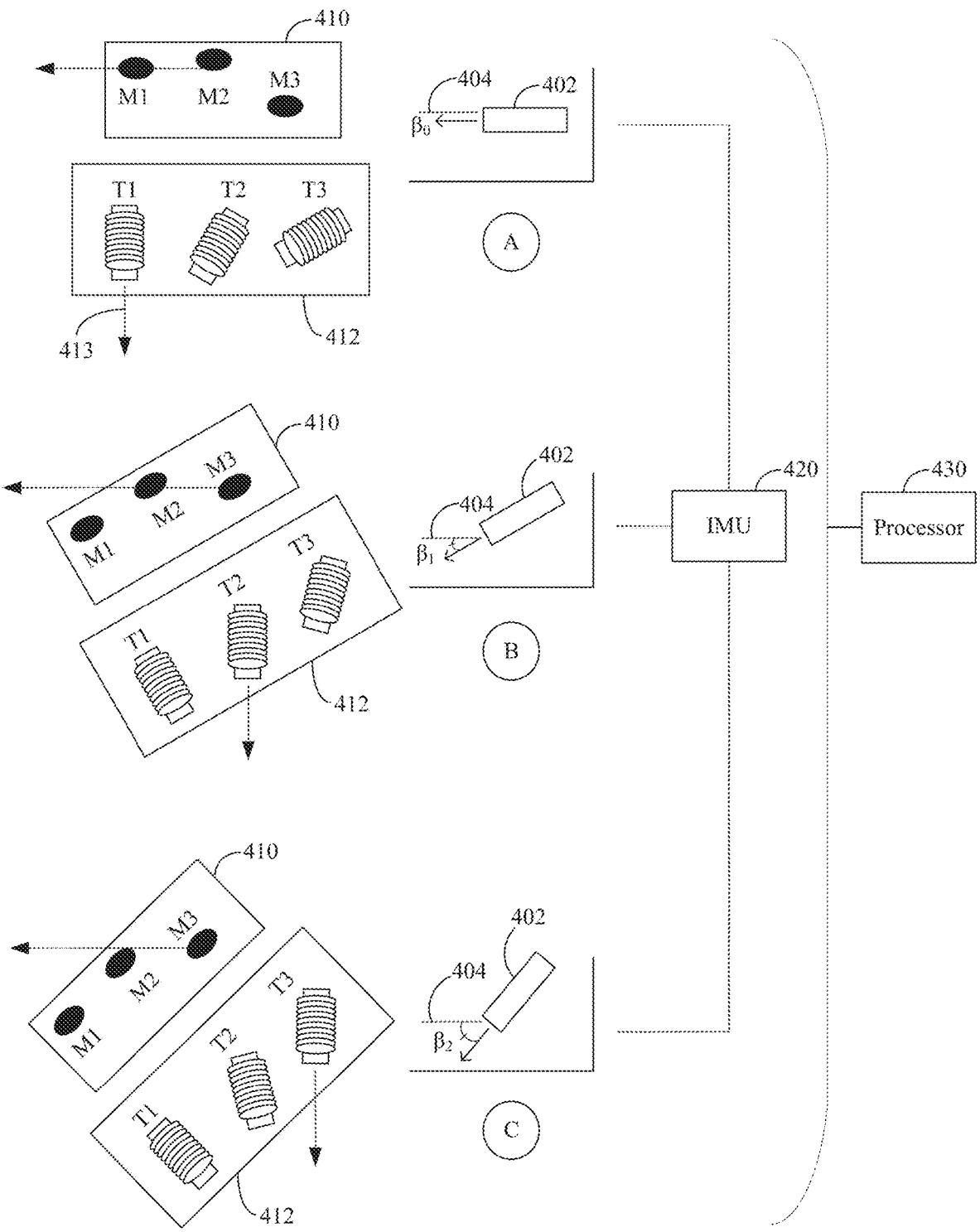
FIG. 4 illustrates a hearing device oriented in different angular positions relative to a horizontal plane which is orthogonal to a direction of gravity, the hearing device configured to provide improved performance when operating in suboptimal angular positions according to any of the disclosed embodiments.

FIG. 4 illustrates hearing device 402 oriented in different angular positions relative to a horizontal plane 404 which is orthogonal to a direction of gravity. In scenario A, the hearing device 402 is oriented in a prescribed (e.g., optimal) angular position for operation relative to the horizontal plane 404. In scenarios B and C, the hearing device 402 is oriented in progressively suboptimal angular positions for operation relative to the horizontal plane 404. For purposes of illustration, and not of limitation, the hearing device 402 includes a microphone arrangement 410 comprising three microphones, M1, M2, M3. The hearing device 402 also includes a telecoil arrangement 412 comprising three telecoils, T1, T2, T3. It is understood that the number of microphones and telecoils can be the same or different, ranging between 1 and 5, for example. The hearing device 402 includes an IMU 420 configured to measure the angular position of the hearing device 402. The IMU 420 can be representative of any one or combination of position and/or motion sensors, such as any combination of one or more accelerometers, gyroscopes, and magnetometers. A processor 430 of the hearing device 402 and/or a processor of a peripheral or accessory device is operatively coupled to the IMU 420, the microphone arrangement 410, and the telecoil arrangement 412.

Microphones M1 and M2 are situated on the hearing device 402 to provide a sensitivity pattern which is forward focused (e.g., substantially parallel to the horizontal plane 404) when the wearer's head is positioned at an optimal position, such as that shown in FIG. 2. Microphone M3 is positioned out-of-plane relative to a plane of microphones M1 and M2. Telecoils T1, T2, T3 have longitudinal axes 413 oriented at different angles relative to a plane parallel to a direction of gravity. For example, the longitudinal axes 413 can be oriented at different angles ranging between 0 and 90° relative to the plane parallel to the direction of gravity.

In scenario A, the angular position of the hearing device 402 is substantially parallel to the horizontal plane 404, in which case an angle, $\beta_0$, measured by IMU 420 is substantially zero degrees. In this scenario, the processor 430 is configured to select microphones M1 and M2 and telecoil T1 for operation, in which case signals produced by microphones M1 and M2 and telecoil T1 are received and processed by the processor 430. In scenario B, the angular position of the hearing device 402 is suboptimal due to flexion of the wearer's neck or hunched/stooped posture of the wearer resulting in a relatively large angle, $\beta_1$, as measured by the IMU 420. In this scenario, the processor 430 is configured to implement a corrective action by changing the directional polar pattern of the microphone arrangement 410 and selecting telecoil T2 for operation. In this scenario, signals produced by microphones M2 and M3 and telecoil T2 are received and processed by the processor 430. In scenario C, the angular position of the hearing device 402 is more suboptimal than in scenario B due to more excessive flexion of the wearer's neck or hunched/stooped posture of the wearer resulting in a relatively large angle, $\beta_2$, as measured by the IMU 420. In this scenario, the processor 430 is configured to implement a corrective action by selecting microphones M2 and M3, and telecoil T3, for operation, in which case signals produced by microphones M2 and M3 and telecoil T3 are received and processed by the processor 430.

Figure 5:
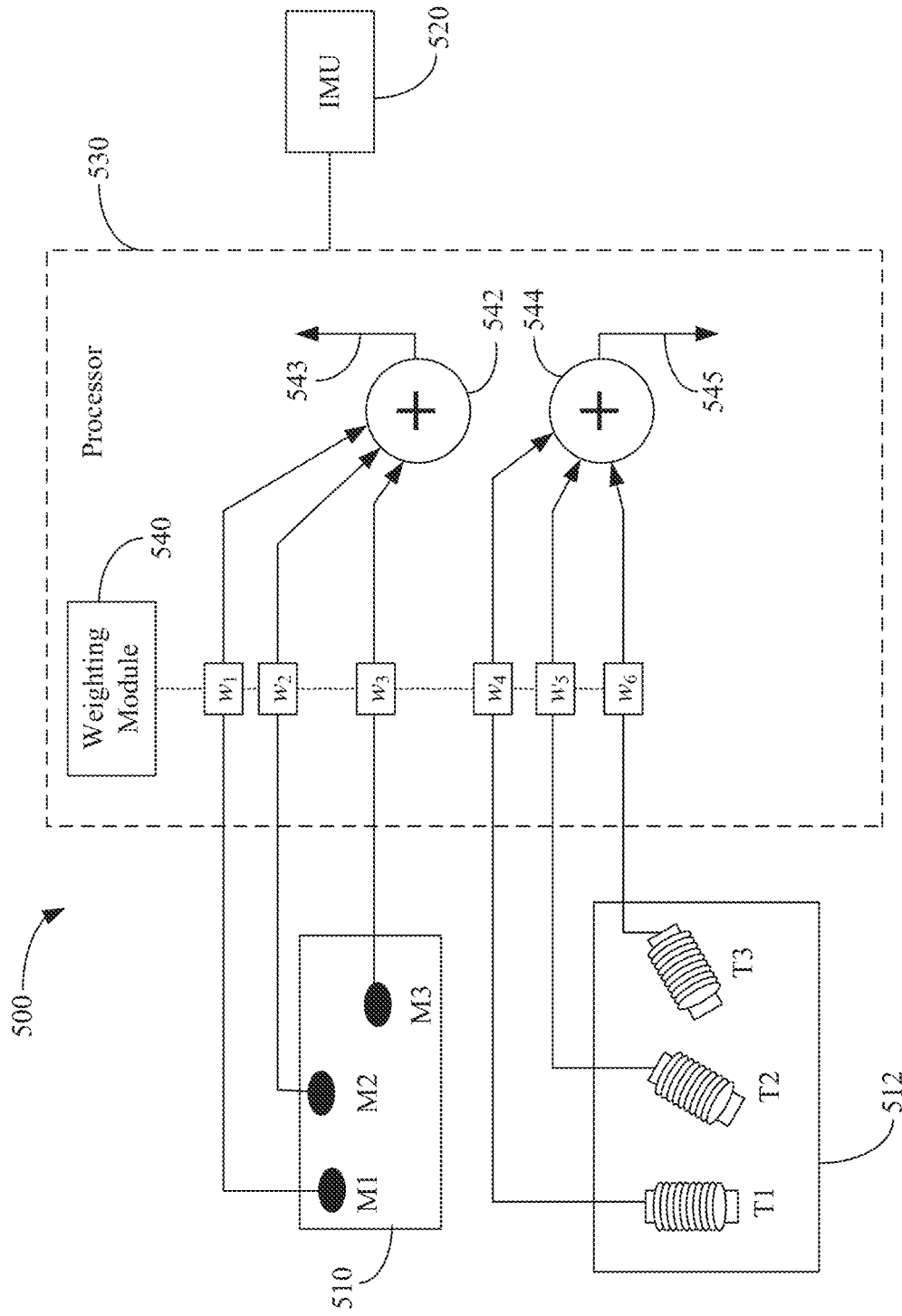
FIG. 5 illustrates various components of a hearing device configured to process multiple microphone signals and multiple telecoil signals in accordance with any of the embodiments disclosed herein.

FIG. 5 illustrates various components of a hearing device 500 configured to process multiple microphone signals and multiple telecoil signals in accordance with any of the embodiments disclosed herein. The hearing device 500 shown in FIG. 5 includes a microphone arrangement 510 comprising three microphones M1, M2, M3. The hearing device 500 also includes a telecoil arrangement 512 comprising three telecoils T1, T2, T3. It is understood that the number of microphones and telecoils can be the same or different, ranging between 1 and 5, for example. The hearing device 500 further includes a processor 530 operatively coupled to an IMU 520, the microphone arrangement 510 and the telecoil arrangement 512. The IMU 520 can be representative of any one or combination of position and/or motion sensors, such as any combination of one or more accelerometers, gyroscopes, and magnetometers. The processor 530 includes a weighting module 540, a first summing device 542, and a second summing device 544.

The processor 530 is configured to implement a corrective action that improves performance of the hearing device 500 in response to detecting a suboptimal angular position of the hearing device 500 (via the IMU 520) relative to the horizontal plane oriented orthogonal to a direction of gravity. As was discussed previously, the processor 530 can be configured to implement a corrective action by activating selected microphones M1, M2, M3 as a function of angular position of the hearing device 500 as measured by the IMU 520. The processor 530 can also be configured to implement the corrective action by receiving signals from selected telecoils T1, T2, T3 as a function of angular position of the hearing device 500 as measured by the IMU 520.

The processor 530 can be configured to alter a mathematical weighting (e.g., via weights $w_1, w_2, w_3, \ldots w_n$) of one or more of the microphone inputs to the first summing device 542 as a function of angular position of the hearing device 500 as measured by the IMU 520. Additionally or alternatively, the processor 530 can be configured to alter a mathematical weighting (via weights $w_4, w_5, w_6, \ldots w_n$) of one or more of the telecoil inputs to the second summing device 544 as a function of angular position of the hearing device 500 as measured by the IMU 520. For example, a weighted contribution to the summed microphone signal 543 by out-of-plane microphone M3 can increase proportionally as a function of the angular position of the hearing device 500 as the device 500 changes from an angular position substantially parallel to the horizontal plane to an angular position directed towards the ground. Similarly, a weighted contribution to the summed telecoil signal 545 by telecoil T3 can increase proportionally as a function of the angular position of the hearing device 500 as the device 500 changes from an angular position substantially parallel to the horizontal plane to an angular position directed towards the ground. Microphone and telecoil signals 543, 545 output from the first and second summing devices 542, 544 can be further processed by the processor 530 and/or other circuitry of the hearing device 500 (e.g., audio signal processing circuitry, telecoil processing circuitry) to provide enhanced or optimized hearing device performance.

FIGS. 6-10 illustrate various methods for improving the performance of a hearing device based on angular position of the hearing device in accordance with any of the embodiments disclosed herein. For example, the methods shown in FIGS. 6-10 can be implemented by any of the hearing devices illustrated in FIGS. 1A, 1B, and 3-5.

Figure 6:
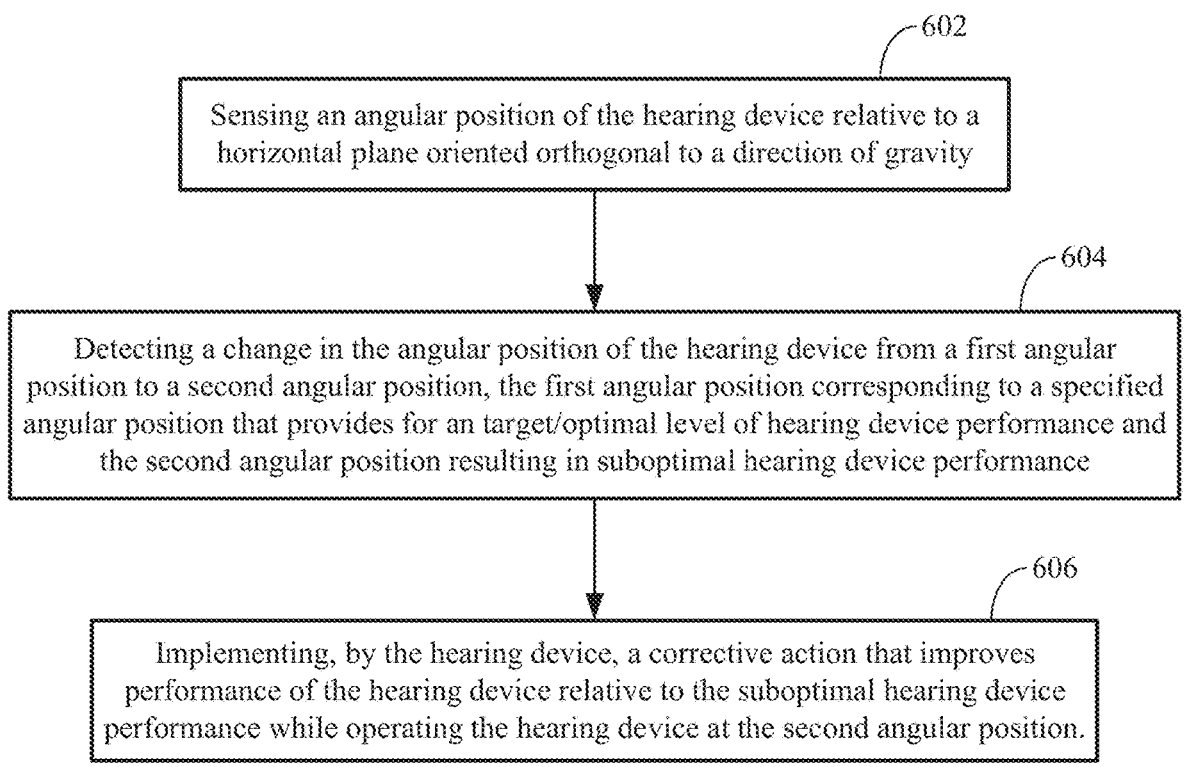
FIG. 6 illustrates a method for improving the performance of a hearing device based on angular position of the device in accordance with any of the embodiments disclosed herein.

FIG. 6 illustrates a method for improving the performance of a hearing device based on angular position of the device in accordance with any of the embodiments disclosed herein. The method shown in FIG. 6 involves sensing 602 an angular position of the hearing device relative to a horizontal plane oriented orthogonal to a direction of gravity. The method involves detecting 604 change in the angular position of the hearing device from a first angular position to a second angular position. The first angular position corresponds to a specified angular position (e.g., a predefined or designed angular position in, on, or about the wearer's ear) that provides for a target or optimal level of device performance. The second angular position results in suboptimal hearing device performance. The second angular position can result, for example, from flexion, extension, lateral flexion, and/or lateral extension of the wearer's neck during operation of the hearing device. The method also involves implementing 606, by the hearing device, a corrective action that improves performance of the hearing device relative to the suboptimal device performance while operating the device at the second angular position.

The method shown in FIG. 6 and other figures can involve comparing one or more performance parameters of the hearing device at the second angular position to corresponding one or more performance parameters of the hearing device associated with the target/optimal level of device performance. For example, the method may involve measuring the SNR or signal strength of one or more microphones, telecoils or other magnetic sensors of the hearing device to determine that the hearing device is in a suboptimal position. The method may involve implementing the corrective action by the hearing device in response to the comparison crossing a predetermined threshold (e.g., a predetermined difference in SNR or signal strength measurements).

Figure 7:
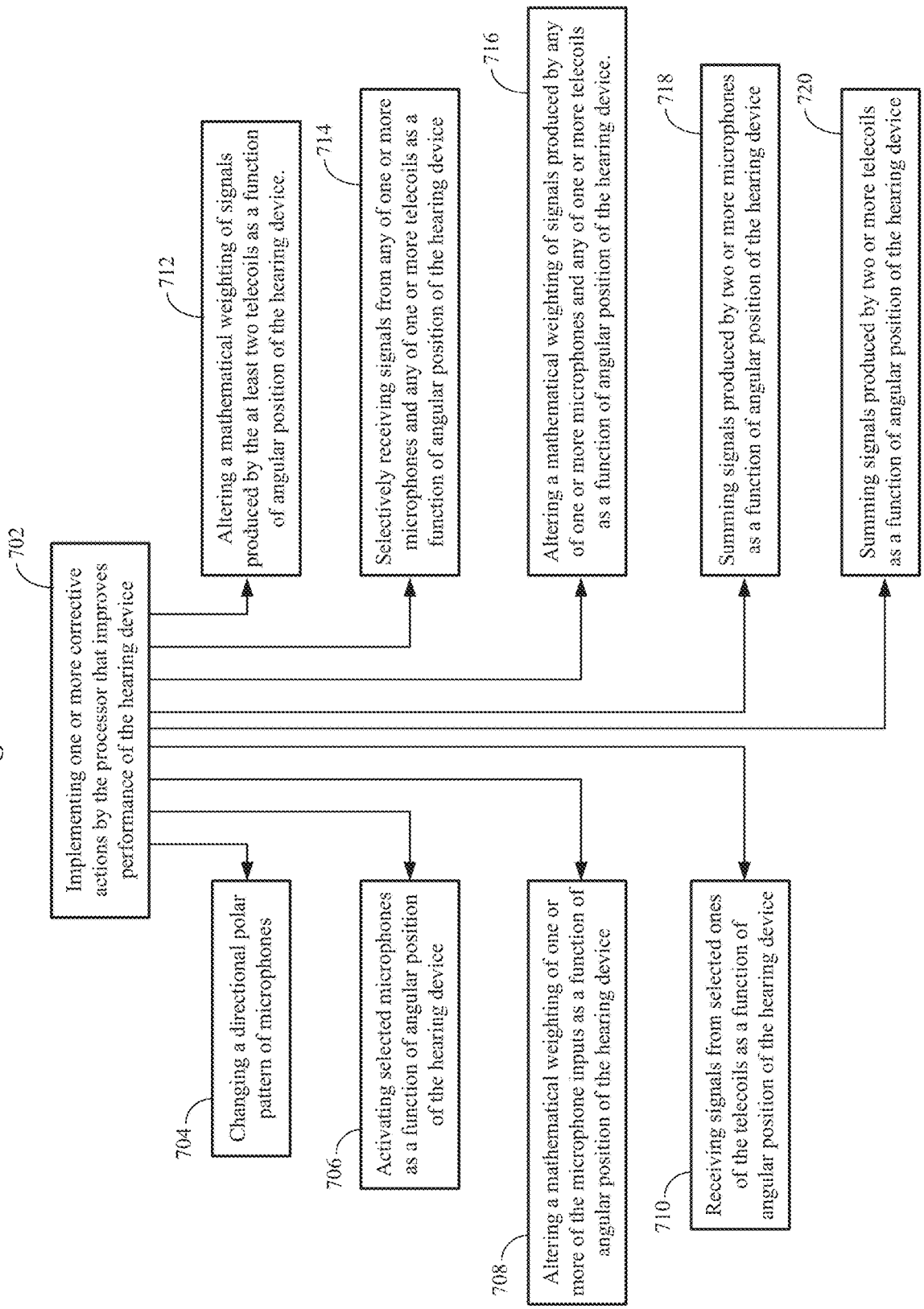
FIG. 7 illustrates a method for improving the performance of a hearing device based on angular position of the device in accordance with any of the embodiments disclosed herein.

FIG. 7 illustrates a method for improving the performance of a hearing device based on angular position of the device in accordance with any of the embodiments disclosed herein. The method shown in FIG. 7 involves implementing 702 one or more corrective actions by the processor of the hearing device and/or a processor of a peripheral or accessory device that improves hearing device performance. The one or more corrective actions implemented by the hearing device processor and/or a processor of a peripheral or accessory device can be performed sequentially or concurrently. For example, some corrective actions can be implemented simultaneously, while other corrective actions can be implemented sequentially by the hearing device processor and/or a processor of a peripheral or accessory device.

A corrective action implemented by the hearing device processor and/or a processor of a peripheral or accessory device can include changing 704 a directional polar pattern of two or more microphones of the hearing device. A corrective action can involve activating 706 selected microphones as a function of angular position of the hearing device. A corrective action can further involve altering 708 a mathematical weighting of one or more of the microphone inputs as a function of angular position of the hearing device. A corrective action can involve receiving 710 signals from selected ones of the telecoils as a function of angular position of the hearing device. A corrective action can include altering 712 a mathematical weighting of signals produced by at least two telecoils as a function of angular position of the hearing device.

A corrective action implemented by the hearing device processor and/or a processor of a peripheral or accessory device can involve selectively receiving 714 signals from any one or more microphones and any one or more telecoils as a function of angular position of the hearing device. A corrective action can involve altering 716 a mathematical weighting of signals produced by any one or more microphones and any one or more telecoils as a function of angular position of the hearing device. A corrective action can also involve summing 718 signals produced by two or more microphones as a function of angular position of the hearing device. A corrective action can further involve summing 720 signals produced by two or more telecoils as a function of angular position of the hearing device. A corrective action implemented by the hearing device processor and/or a processor of a peripheral or accessory device can involve summing of microphone signals and summing of telecoil signals as a function of angular position of the hearing device as described in blocks 718 and 720.

Figure 8:
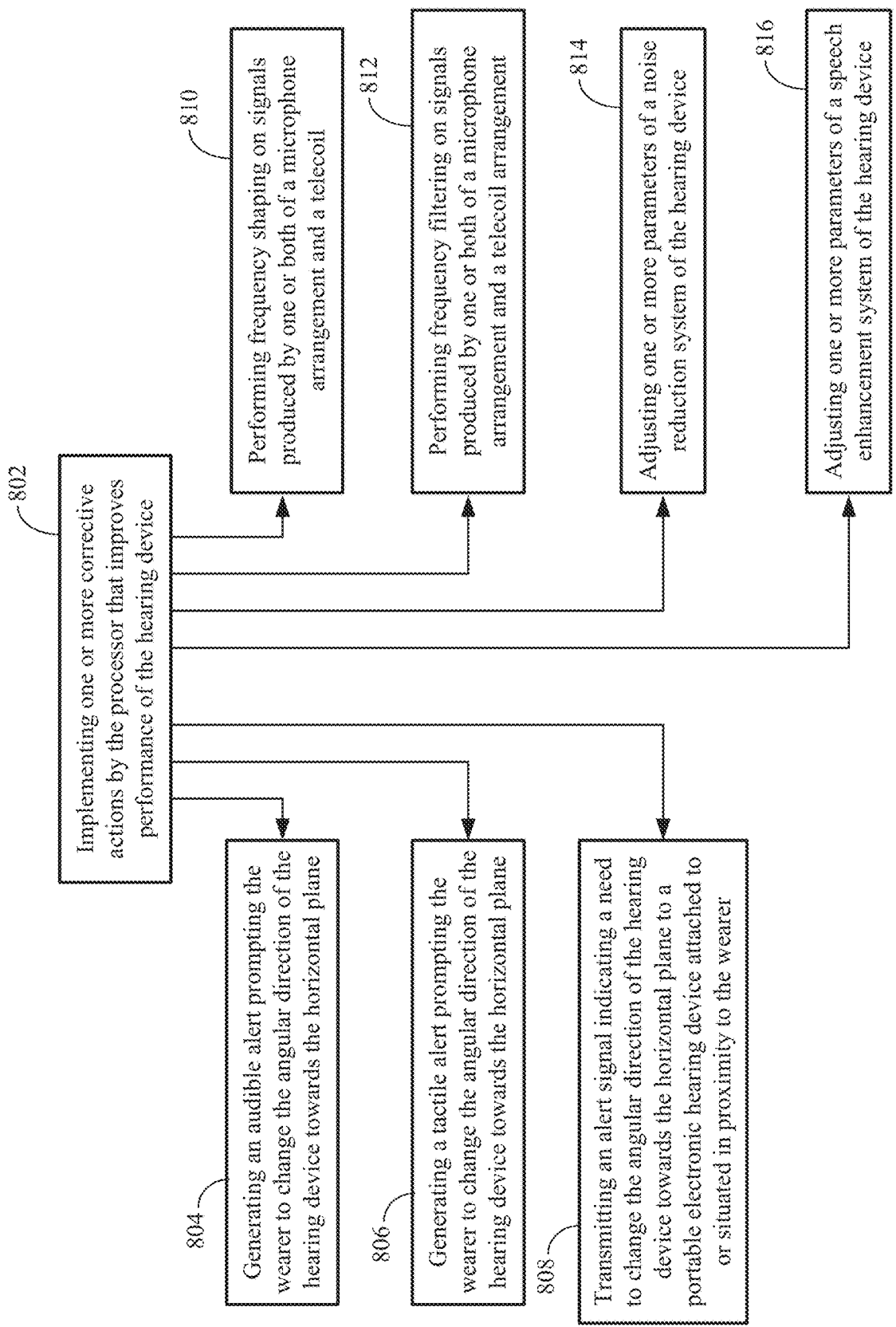
FIG. 8 illustrates a method for improving the performance of a hearing device based on angular position of the device in accordance with any of the embodiments disclosed herein.

FIG. 8 illustrates a method for improving the performance of a hearing device based on angular position of the device in accordance with any of the embodiments disclosed herein. The method shown in FIG. 8 involves implementing 802 one or more corrective actions by the processor of the hearing device and/or a processor of a peripheral or accessory device that improves for device performance. The one or more corrective actions implemented by the hearing device processor and/or a processor of a peripheral or accessory device can be performed sequentially or concurrently. For example, some corrective actions can be implemented simultaneously, while other corrective actions can be implemented sequentially by the hearing device processor and/or a processor of a peripheral or accessory device. A corrective action implemented by the hearing device processor and/or a processor of a peripheral or accessory device can include generating 804 an audible alert prompting the wearer to change the angular direction of the device towards a horizontal plane which is orthogonal to a direction of gravity. The one or more corrective actions can include generating 806 a tactile alert prompting the wearer to change the angular direction of the device towards the horizontal plane. A corrective action can involve transmitting 808 an alert signal indicating a need to change angular direction of the hearing device towards the horizontal plane to a portable electronic device attached to or situated in proximity to the wearer.

A corrective action implemented by the hearing device processor and/or a processor of a peripheral or accessory device can include performing 810 frequency shaping on signals produced by one or both of a microphone arrangement and a telecoil arrangement. A corrective action can include performing 812 frequency filtering on signals produced by one or both of the microphone arrangement and the telecoil arrangement of the hearing device. A corrective action can involve adjusting 814 one or more parameters of a noise reduction system of the hearing device. For example, the hearing device processor can be configured to adjust one or more parameters of a noise reduction system that implements Fast Signal Mic Noise Reduction (FSMNR), spectral subtraction, spectral subtraction with over subtraction model, non-linear spectral subtraction, adaptive noise cancellation, Winer filtering, Kalman filtering, and beamforming noise suppression, for example. A corrective action implemented by the hearing device processor can include adjusting 816 one or more parameters of a speech enhancement system of the hearing device. For example, the hearing device processor and/or a processor of a peripheral or accessory device can be configured to adjust one or more parameters of a speech enhancement system that implements a frequency lowering/shifting technique, phoneme augmentation, linear predictive coding, and signal subspace methods, for example.

Figure 9:
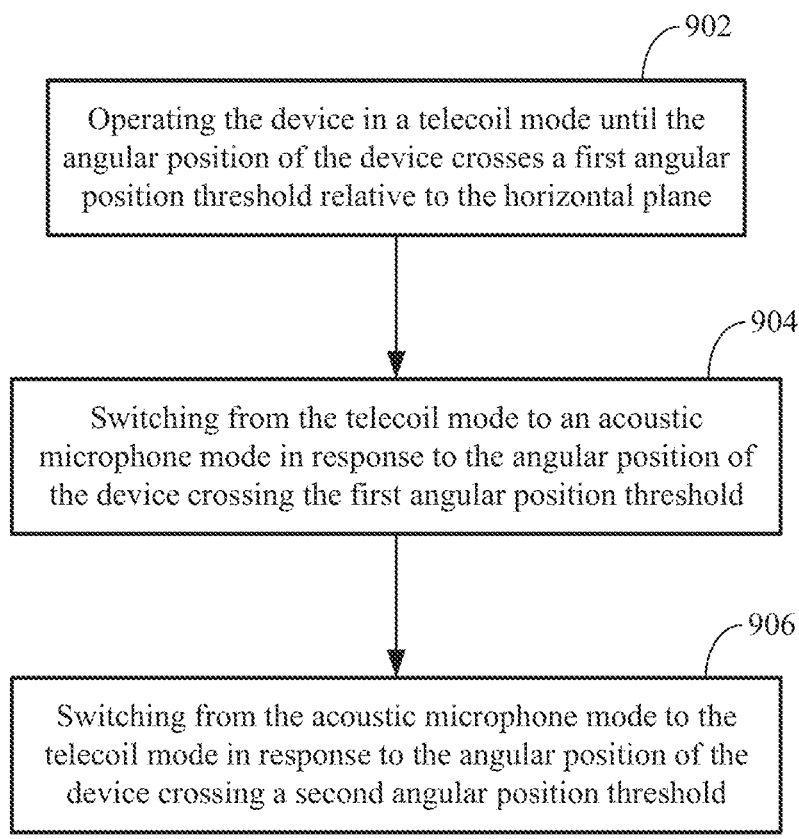
FIG. 9 illustrates a method for improving the performance of a hearing device based on angular position of the device in accordance with any of the embodiments disclosed herein.

FIG. 9 illustrates a method for improving the performance of a hearing device based on angular position of the device in accordance with any of the embodiments disclosed herein. The method shown in FIG. 9 involves operating 902 the hearing device exclusively or predominately in a telecoil mode until the angular position of the hearing device crosses a first angular position threshold relative to a horizontal plane which is orthogonal to a direction of gravity. The method involves switching 904 from the telecoil mode to an acoustic microphone mode and operating the device exclusively or predominately in the acoustic microphone mode in response to the angular position of the hearing device crossing the first angular position threshold. The method also involves switching 906 from the acoustic microphone mode to the telecoil mode and operating the device exclusively or predominately in a telecoil mode in response to the angular position of the device crossing a second angular position threshold. During each of the three operating phases 902, 904, 906, performance of the hearing device may involve a mix of signals from the telecoil and microphone arrangements, hence the use of the term "predominately operating" in the telecoil mode (which can involve use of microphone signals) and "predominately operating" in the acoustic microphone mode (which can involve use of telecoil signals).

Figure 10:
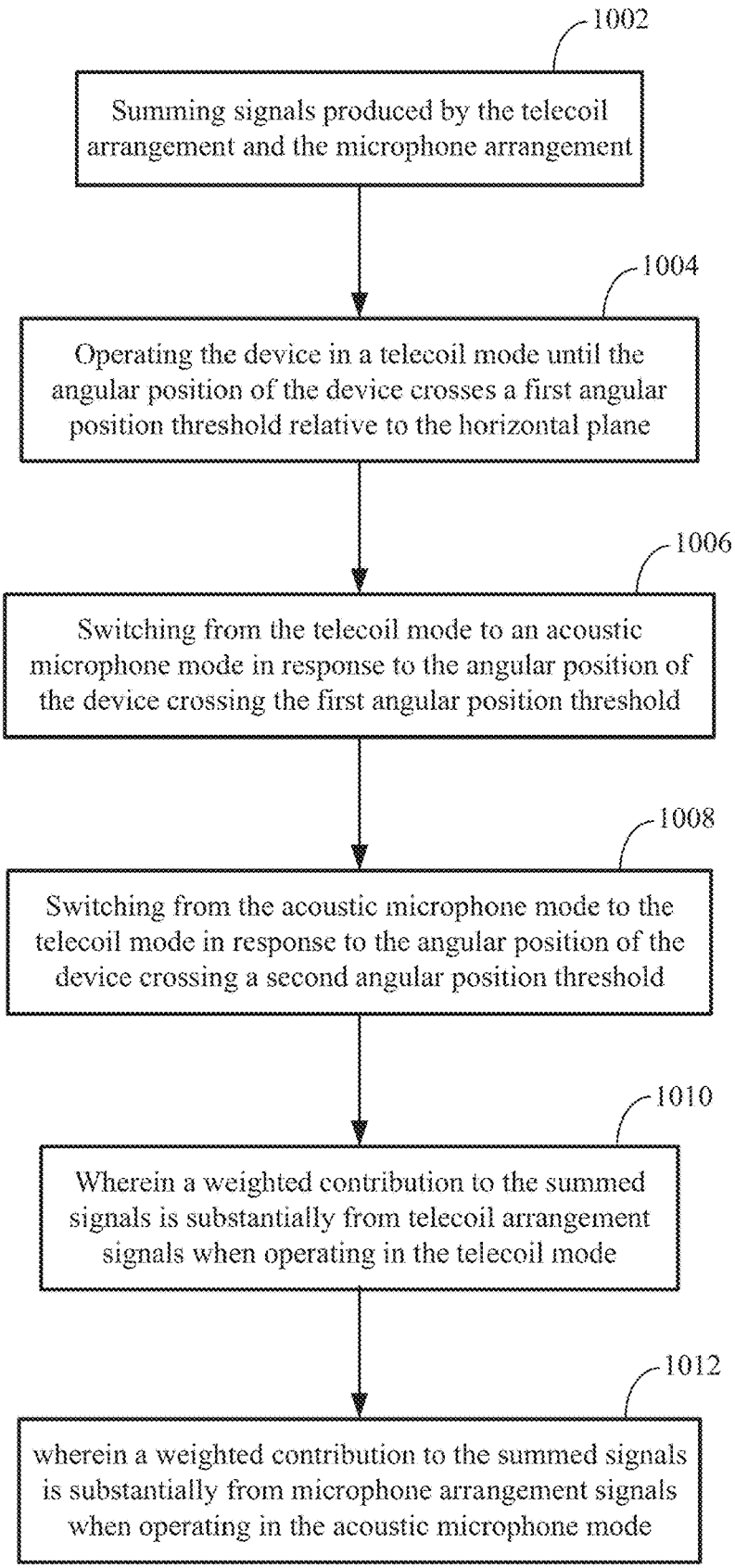
FIG. 10 illustrates a method for improving the performance of a hearing device based on angular position of the device in accordance with any of the embodiments disclosed herein.

FIG. 10 illustrates a method for improving the performance of a hearing device based on angular position of the device in accordance with any of the embodiments disclosed herein. The method shown in FIG. 10 involves summing 1002 signals produced by a telecoil arrangement and a microphone arrangement the hearing device. The method involves operating 1004 the hearing device in a telecoil mode until the angular position of the device crosses a first angular position threshold relative to a horizontal plane which is orthogonal to a direction of gravity. The method also involves switching 1006 from the telecoil mode to an acoustic microphone mode in response to the angular position of the device crossing the first angular position threshold. The method further involve switching 1008 from the acoustic microphone mode to the telecoil mode in response to the angular position of the hearing device crossing a second angular position threshold.

The method also involves weighting signals from the telecoil arrangement and the microphone arrangement based on the angular position of the hearing device. According to the method shown in FIG. 10, a weighted contribution to the summed signals 1010 is substantially from telecoil arrangement signals when operating in the telecoil mode. Also according to the method shown in FIG. 10, a weighted contribution to the summed signals 1012 is substantially from microphone arrangement signals when operating in the acoustic microphone mode. The method shown in FIG. 10 can be implemented by a processor of the hearing device and/or a processor of a peripheral or accessory device.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "operatively coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably operatively coupled to an antenna element to provide a radio frequency electromagnetic signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise. As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. An ear-worn electronic hearing device configured for use in, on, or about an ear of a wearer, the device comprising:
    a processor operatively coupled to memory;
    a speaker or a receiver operatively coupled to the processor;
    one or both of a microphone arrangement and a telecoil arrangement operatively coupled to the processor to provide one or more inputs to the processor; and
    a sensor operatively coupled to the processor and configured to sense an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane;
    wherein the processor is configured to:
        detect a change in the angular position of the device from a first angular position to a second angular position; and
        implement, based on at least one of the one or more inputs or the second angular position, one or more corrective actions that improves performance of the device while operating the device at the second angular position.

2. The device of claim 1, wherein the processor is configured to:
    determine the first angular position of the device by determining an orientation of the wearer's head in a direction substantially along the horizontal plane; and
    determine the second angular position of the device by determining the orientation of the wearer's head in a direction towards the ground.

3. The device of claim 1, wherein the processor is configured to:
    compare one or more performance parameters of the device at the second angular position to corresponding one or more performance parameters of the device associated with a target or optimal level of device performance; and
    implement the corrective action in response to the comparison crossing a predetermined threshold.

4. The device of claim 1, wherein the processor is configured to implement the one or more corrective actions while operating the device at the second angular position in response to the device having excessive performance while operating at the second angular position relative to the first angular position.

5. The device of claim 1, wherein the processor is configured to implement the corrective action by one or more of:
    changing a directional polar pattern of a microphone array of the device;
    activating selected microphones of the device as a function of angular position of the device;
    altering a mathematical weighting of one or more of microphone inputs as a function of angular position of the device;
    receiving signals from selected telecoils of the device as a function of angular position of the device;
    altering a mathematical weighting of signals produced by at least two telecoils of the device as a function of angular position of the device;
    selectively receiving signals from any of one or more microphones and any of one or more telecoils of the device as a function of angular position of the device; and
    altering a mathematical weighting of signals produced by any of one or more microphones and any one or more telecoils of the device as a function of angular position of the device.

6. The device of claim 1, wherein:
    the device comprises first and second microphones situated on a first plane of the device and a third microphone situated on a second plane of the device transverse to the first plane;
    the processor is configured to implement the corrective action by summing signals produced by the first, second, and third microphones as a function of angular position of the device; and
    contribution to the summed signals by the third microphone increases as the angular position of the device changes from the first angular position towards the second angular position.

7. The device of claim 1, wherein the device comprises a telecoil arrangement and a microphone arrangement, and the processor is configured to implement the corrective action by:
    operating the device predominately in a telecoil mode until the angular position of the device reaches a threshold angular position relative to the horizontal plane;
    switching from the telecoil mode to an acoustic microphone mode and operating the device predominately in the acoustic microphone mode in response to the angular position of the device exceeding the threshold angular position; and
    switching from the acoustic microphone mode to the telecoil mode and operating the device predominately in the telecoil mode in response to the angular position of the device no longer exceeding the threshold angular position.

8. The device of claim 1, wherein the processor is configured to implement the corrective action by one of more of:
    generating an audible alert prompting the wearer to change the angular direction of the device towards the horizontal plane;
    generating a tactile alert prompting the wearer to change the angular direction of the device towards the horizontal plane; and
    generating an alert signal indicating a need to change the angular direction of the device towards the horizontal plane and transmitting the alert signal to a portable electronic device attached to or situated in proximity to the wearer.

9. The device of claim 1, wherein the processor is configured to implement the corrective action by one or more of:
- performing frequency shaping on signals produced by one or both of a microphone arrangement and a telecoil arrangement of the device;
- performing frequency filtering on signals produced by one or both of the microphone arrangement and the telecoil arrangement of the device;
- adjusting one or more parameters of a noise reduction system of the device; and
- adjusting one or more parameters of a speech enhancement system of the device.

10. The device of claim 1, wherein the sensor comprises one or more of:
- one or more inertial sensors;
- one or more magnetic sensors;
- an altimeter or a barometer implemented by the processor configured to process microphone signals to detect changes in altitude or barometric pressure between microphones of a microphone arrangement; and
- the processor configured to sense changes in signal strength or signal-to-noise ratio using signals produced by the microphone arrangement, a telecoil arrangement of the device, or the sensor of the device.

11. The device of claim 1, wherein the processor is configured to determine the angular position of the device using one or both of a positional sensor and a motion sensor.

12. A method implemented by an ear-worn electronic device situated in, on, or about an ear of a wearer, the method comprising:
- sensing an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane;
- detecting a change in the angular position of the device from a first angular position to a second angular position; and
- implementing, based on the second angular position, one or more corrective actions that improves performance of the device while operating the device at the second angular position.

13. The method of claim 12, wherein:
- the first angular position of the device is determined by the orientation of the wearer's head in a direction substantially along the horizontal plane; and
- the second angular position of the device is determined by the orientation of the wearer's head in a direction towards the ground.

14. The method of claim 12, comprising:
- comparing one or more performance parameters of the device at the second angular position to corresponding one or more performance parameters of the device associated with a target or optimal level of device performance; and
- implementing the corrective action by the device in response to the comparison crossing a predetermined threshold.

15. The method of claim 12, wherein the one or more corrective actions are implemented while operating the device at the second angular position in response to the device having excessive performance while operating the device at the second angular position relative to the first angular position.

16. The method of claim 12, wherein implementing the corrective action comprises one or more of:
- changing a directional polar pattern of a microphone array of the device;
- activating selected microphones of the device as a function of angular position of the device;
- altering a mathematical weighting of one or more of microphone inputs as a function of angular position of the device;
- receiving signals from selected telecoils of the device as a function of angular position of the device;
- altering a mathematical weighting of signals produced by at least two telecoils of the device as a function of angular position of the device;
- selectively receiving signals from any of one or more microphones and any of one or more telecoils of the device as a function of angular position of the device; and
- altering a mathematical weighting of signals produced by any of one or more microphones and any one or more telecoils of the device as a function of angular position of the device.

17. The method of claim 12, wherein implementing the corrective action comprises one or more of:
- generating an audible alert prompting the wearer to change the angular direction of the device towards the horizontal plane;
- generating a tactile alert prompting the wearer to change the angular direction of the device towards the horizontal plane; and
- generating an alert signal indicating a need to change the angular direction of the device towards the horizontal plane and transmitting the alert signal to a portable electronic device attached to or situated in proximity to the wearer.

18. An ear-worn electronic hearing device configured for use in, on, or about an ear of a wearer, the device comprising:
- a processor operatively coupled to memory;
- a speaker or a receiver operatively coupled to the processor;
- a microphone arrangement and a telecoil arrangement operatively coupled to the processor to provide one or more inputs to the processor;
- a sensor operatively coupled to the processor and configured to sense an angular position of the device relative to a horizontal plane oriented orthogonal to a direction of gravity, the angular position of the device substantially corresponding to an orientation of the wearer's head relative to the horizontal plane, a longitudinal plane orthogonal to the horizontal plane, and a frontal plane orthogonal to the horizontal plane and the longitudinal plane;
- wherein the processor is configured to:
  - detect a change in the angular position of the device from a first angular position to a second angular position; and
  - implement, based on at least one of the one or more inputs or the second angular position, one or more corrective actions that improves performance of the device while operating the device at the second angular position.

19. The device of claim 18, wherein:

the device comprises at least one microphone and at least one telecoil; and the processor is configured to implement the corrective action in response to selectively receiving signals from any of the at least one microphone and any of the at least one telecoil as a function of angular position of the device.

20. The device of claim 18, wherein:

the device comprises first and second microphones situated on a first plane of the device and a third microphone situated on a second plane of the device transverse to the first plane; and the processor is configured to implement the corrective action by summing signals produced by the first, second, and third microphones as a function of angular position of the device.

21. The device of claim 18, wherein the processor is configured to implement the one or more corrective actions while operating the device at the second angular position in response to the device having excessive performance while operating at the second angular position relative to the first angular position.

\* \* \* \* \*